United States Patent
Jun et al.

(10) Patent No.: US 8,524,119 B2
(45) Date of Patent: Sep. 3, 2013

(54) CATALYST FOR PREPARING SYNTHESIS GAS FROM NATURAL GAS AND CARBON DIOXIDE, AND PREPARATION METHOD THEREOF

(75) Inventors: Ki Won Jun, Daejeon (KR); Seung-Chan Baek, Daejeon (KR); Jong Wook Bae, Daejeon (KR); Keh-Sik Min, Seoul (KR); Seok-Lyong Song, Ulsan (KR); Tae-Young Oh, Ulsan (KR)

(73) Assignees: Hyundai Heavy Industries Co., Ltd., Ulsan (KR); Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 13/055,853

(22) PCT Filed: Jul. 30, 2009

(86) PCT No.: PCT/KR2009/004256
§ 371 (c)(1),
(2), (4) Date: Jan. 25, 2011

(87) PCT Pub. No.: WO2010/013958
PCT Pub. Date: Feb. 4, 2010

(65) Prior Publication Data
US 2011/0114892 A1  May 19, 2011

(30) Foreign Application Priority Data
Aug. 1, 2008 (KR) .......................... 1020080075787

(51) Int. Cl.
C01B 3/26 (2006.01)
(52) U.S. Cl.
USPC ............................ 252/373; 423/651; 423/652
(58) Field of Classification Search
USPC .................................. 423/650–654; 252/373
See application file for complete search history.

(56) References Cited

U.S. PATENT DOCUMENTS

| 4,581,157 A | * | 4/1986 | Twigg | 252/373 |
| 5,039,510 A | * | 8/1991 | Pinto | 423/652 |

(Continued)

FOREIGN PATENT DOCUMENTS

| CN | 1232720 A | 10/1999 |
| CN | 101049566 | * 10/2007 |

(Continued)

OTHER PUBLICATIONS

G.C. Chinchen et al., "The Activity and State of the Copper Surface in Methanol Synthesis Catalysts", Applied Catalysis, 1986, pp. 101-107, vol. 25.

(Continued)

*Primary Examiner* — Wayne Langel
(74) *Attorney, Agent, or Firm* — Dickstein Shapiro LLP

(57) ABSTRACT

Disclosed are a catalyst for preparing synthesis gas from natural gas and carbon dioxide, and a method for preparing the same. More particularly, a combined reforming process is performed as an economical way of using carbon dioxide, wherein steam reforming of natural gas is carried out simultaneously with carbon dioxide reforming of methane in such a manner that a predetermined ratio of carbon monoxide/carbon dioxide/hydrogen ($H_2/(2CO+3CO_2)$=0.85-1.15) is maintained. In this manner, the catalyst is used to prepare synthesis gas suitable for methanol synthesis and Fischer-Tropsch synthesis. Disclosed also is a method for preparing synthesis gas on a specific catalyst consisting of Ni/Ce/MgAlOx or Ni/Ce-Zr/MgAlOx. The catalyst is inhibited from deactivation caused by generation of cokes during the reaction as well as deactivation caused by reoxidation of nickel with water added during the reaction. Therefore, the catalyst shows excellent activity as compared to other catalysts for use in combined reforming.

2 Claims, 2 Drawing Sheets

(56) References Cited

U.S. PATENT DOCUMENTS

| | | | |
|---|---|---|---|
| 5,118,715 A | 6/1992 | Iglesia et al. | |
| 5,980,840 A * | 11/1999 | Kleefisch et al. | 422/211 |
| 6,348,278 B1 * | 2/2002 | LaPierre et al. | 429/411 |
| 6,416,731 B1 * | 7/2002 | Dohrup et al. | 423/653 |
| 6,726,853 B2 * | 4/2004 | Okado et al. | 252/373 |
| 7,544,346 B2 * | 6/2009 | Krause et al. | 423/650 |
| 8,142,756 B1 * | 3/2012 | Gardner et al. | 423/651 |
| 2002/0098129 A1 * | 7/2002 | Martin et al. | 422/173 |
| 2002/0146359 A1 * | 10/2002 | Lomax et al. | 422/198 |
| 2003/0032554 A1 * | 2/2003 | Park et al. | 502/302 |
| 2004/0014600 A1 * | 1/2004 | Fukunaga | 502/304 |
| 2004/0067848 A1 | 4/2004 | Wakatsuki et al. | |
| 2005/0265920 A1 * | 12/2005 | Ercan et al. | 423/651 |
| 2007/0036713 A1 * | 2/2007 | Kobayashi et al. | 423/652 |
| 2007/0167323 A1 * | 7/2007 | Kobayashi | 502/341 |
| 2007/0172416 A1 * | 7/2007 | Kawashima et al. | 423/648.1 |

FOREIGN PATENT DOCUMENTS

| | | | |
|---|---|---|---|
| EP | 1 013 603 A1 | | 6/2000 |
| GB | 2213496 | * | 12/1987 |
| JP | 2004-66170 A | | 3/2004 |
| JP | 2006-61760 A | | 3/2006 |
| KR | 10-2002-0021721 A | | 3/2002 |
| KR | 10-2002-0088213 A | | 11/2002 |
| KR | 10-2004-0051953 A | | 6/2004 |
| KR | 10-2005-0051820 A | | 6/2005 |
| KR | 10-2006-0132293 A | | 12/2006 |
| KR | 10-2007-0043201 A | | 4/2007 |
| KR | 10-0723392 B1 | | 5/2007 |

OTHER PUBLICATIONS

Deng Jingfa et al., "A novel process for preparation of a Cu/ZnO/Al$_2$O$_3$ ultrafine catalyst for methanol synthesis from CO$_2$+H$_2$: comparison of various preparation methods", Applied Catalysis A: General, 1996, pp. 75-85, vol. 139.

Hengyong Xu et al., "A study of the reforming of natural gas with steam, oxygen and carbon dioxide to produce syngas for methanol feedstock", Journal of Molecular Catalysis A: Chemical, 1999, pp. 41-46, vol. 147.

Aisling M. O'Connor et al., "The effect of O$_2$ addition on the carbon dioxide reforming of methane over Pt/ZrO$_2$ catalysts", Catalysis Today, 1998, pp. 203-210, vol. 46.

F. Frusteri et al., "Potassium-enhanced stability of Ni/MgO catalysts in the dry-reforming of methane", Catalysis Communications, 2001, pp. 49-56, vol. 2.

Rong Zhao et al., "Spray-Dried Iron Fischer-Tropsch Catalysts. 1. Effect of Structure on the Attrition Resistance of the Catalysts in the Calcined State", Ind. Eng. Chem. Res., 2001, pp. 1065-1075, vol. 40.

A. F. Lucrédio et al., "Nickel catalysts Promoted with Cerium and Lanthanum to Reduce Carbon Formation in Partial Oxidation of Methane Reactions," Applied Catalysis A: General, vol. 333, pp. 90-95, 2007.

\* cited by examiner

CATALYST FOR PREPARING SYNTHESIS GAS FROM NATURAL GAS AND CARBON DIOXIDE, AND PREPARATION METHOD THEREOF

TECHNICAL FIELD

The present disclosure relates to a catalyst for preparing synthesis gas from natural gas and carbon dioxide, a method for preparing the same, and a method for preparing synthesis gas for use in methanol synthesis or Fischer-Tropsch synthesis.

BACKGROUND ART

Processes for preparing synthesis gas using natural gas may be classified generally into steam reforming of methane (SRM), partial oxidation of methane (POM), and carbon dioxide reforming of methane (CDR). In each reforming process, the ratio of hydrogen to carbon monoxide ($H_2$/CO) may be varied with the optimal condition required for the subsequent process. For example, in the case of a highly endothermic SRM process, it is possible to obtain a ratio of $H_2$/CO of 3 or higher. Thus, the process is suitable for hydrogen production and ammonia preparation. In the case of POM process, a ratio of $H_2$/CO of about 2 is obtained. Thus, the process is suitable for methanol synthesis and hydrocarbon formation through Fischer-Tropsch synthesis. Hereinafter, the above-mentioned reforming processes are outlined with their advantages, disadvantages and the values of heat of reactions.

Steam Reforming of Methane (SRM)

$$CH_4+H_2O=3H_2+CO \ \Delta H=226 \text{ kJ/mol}$$

→high endothermic reaction, $H_2$/CO>3, excess steam is required.

Partial Oxidation of Methane (POM)

$$CH_4+0.5O_2=2H_2+CO \ \Delta H=-44 \text{ kJ/mol}$$

→mild exothermic reaction, $H_2$/CO=2, $O_2$ production process is required.

Carbon Dioxide Reforming of Methane (CDR)

$$CH_4+CO_2=2H_2+2CO \ \Delta H=261 \text{ kJ/mol}$$

→high endothermic reaction, $H_2$/CO=1, $CO_2$ addition is required.

In addition to the above reforming processes, there are known an auto-thermal reforming (ATR) process including POM combined with SRM, a tri-reforming process including POM combined with SRM and CDR, or the like in order to maintain an adequate $H_2$/CO ratio as well as to increase energy and carbon efficiency. Further, it is possible to obtain synthesis gas having different $H_2$/CO ratios depending on the type of reforming process and catalyst. Recently, many patent applications related to different methods using synthesis gas having such different ratios have been made (Korean Patent Publication Nos. 2006-0132293 and 2005-0051820).

The present disclosure relates to a nickel-based catalyst for combined reforming for preparing synthesis gas, wherein the combined reforming is carried out by SRM combined with CDR, and the synthesis gas is suitable for methanol synthesis and Fischer-Tropsch synthesis. In general, it is known that a ratio of $H_2/(2CO+3CO_2)$ in synthesis gas of about 1.05 is thermodynamically suitable for methanol synthesis. As the ratio increases up to 1.05, methanol yield also increases. Therefore, it is required to add hydrogen or to adjust the conversion in CDR in order to adjust the above ratio. In addition, in the case of Fischer-Tropsch synthesis using an iron-based catalyst, surplus hydrogen is produced during the reaction due to high activity of water gas shift (CO+$H_2O=H_2+CO_2$) reaction and high selectivity toward $CO_2$ is provided. Such iron-based catalysts have their unique high activity, and allow progress of Fischer-Tropsch synthesis even in the presence of a low molar ratio of synthesis gas ($H_2$/CO=0.5-0.7) containing $CO_2$, due to high conversion of water gas.

In the case of a currently available SRM process, a Ni/$Al_2O_3$ catalyst system is used at a reaction temperature of 750-850° C. under a molar ratio of steam/methane of 4-6:1. However, such a catalyst system at low $H_2O/CH_4$ ratio is problematic in that it undergoes severe deactivation caused by carbon deposition. Therefore, to solve that problem, many studies have been conducted about catalyst systems containing noble metals or transition metals and alkali metals as co-catalysts (*Journal of Molecular Catalysis A* 147 (1999) 41).

In the case of a CDR process, more severe deactivation of catalysts occurs due to carbon deposition. Therefore, in order to inhibit such catalyst deactivation, many studies have been conducted about noble metal catalysts (Pt/$ZrO_2$) and Ni/MgO or Ni/MgAl$O_x$ catalyst systems, to which alkali metals are added as co-catalysts (*Catalysis Today* 46 (1998) 203, *Catalysis communications* 2 (2001) 49, and Korean Patent Publication No. 10-2007-0043201). In general, when using commercially available SRM catalysts directly to CDR process and combined CDR and SRM processes, deactivation of catalysts caused by carbon deposition is accelerated. According to our previous studies (Korean Patent Publication Nos. 2002-0021721, 2004-0051953 and 2002-0088213), several methods for inhibiting catalyst deactivation caused by carbon deposition are disclosed, wherein catalysts are prepared by supporting nickel on a zirconia carrier or alumina carrier modified with cerium, or by carrying out co-precipitation of cerium, zirconium and nickel.

According to the present disclosure, nickel used as a catalytically active ingredient is supported on a MgAl$O_x$ metal oxide carrier pretreated with either or both of cerium and zirconium, so that the resultant catalyst is used for combined reforming (SRM+CDR) of methane to produce synthesis gas having a composition suitable for methanol synthesis and Fischer-Tropsch synthesis, while inhibiting deactivation of the catalyst caused by carbon deposition.

Although many workers have participated in studies for improving the quality of methanol synthesis catalysts, complete understanding about the active site of a catalyst for methanol synthesis cannot be accomplished. However, it is known that oxidation state of Cu and redox property of reduced Cu particles play an important role in determining the catalyst quality. It is also known that the activity of a Cu catalyst in a reaction of methanol synthesis is in proportion to the specific surface area of Cu of the metal components. It is reported that coordination, chemisorption, activation of CO and homogeneous $H_2$ splitting occur on $Cu^0$ or $Cu^+$, and non-homogeneous $H_2$ splitting, leading to $H^{\delta+}$ and $H^{\delta-}$ in a catalytic process using a ZnO-containing catalyst, occurs on ZnO (*Appl. Catal. A* 25, (1986) 101). Herein, it is reported that when the molar ratio of Cu/Zn is 8 or more, the specific surface area decreases rapidly (*Appl. Catal. A* 139, (1996) 75). For this reason, Cu is used in combination with Zn to prepare the catalyst, and a molar ratio of Cu/Zn of 3/7 is known to provide the highest activity. However, it is known that when $CO_2$ is present or when the proportion of oxygen-containing materials that cover the $Cu^0$ surface increases, the catalyst activity is independent from the $Cu^0$ surface area. It is also reported that such a phenomenon results from the fact that the $Cu^+$ active site functions as an active site during the methanol synthesis.

Meanwhile, Fischer-Tropsch synthesis provides a product/byproduct distribution that varies with the catalytically active ingredient used therein. In general, iron-based catalysts and cobalt-based catalysts are used. The Fischer-Tropsch processes using iron-based catalysts produce a surplus amount of hydrogen and provide high selectivity toward $CO_2$ due to high conversion of water gas ($CO+H_2O=H_2O+CO_2$). However, such iron-based catalysts used in Fischer-Tropsch synthesis are cheaper than cobalt, have specifically high activity, and allow progress of Fischer-Tropsch synthesis even under a low molar ratio of synthesis gas ($H_2/CO=0.5$-$0.7$) containing $CO_2$ due to high activity of water gas shift reaction. Therefore, due to high activity toward water gas conversion, such Fischer-Tropsch processes using iron-based catalysts are advantageous in treating synthesis gas having a low $H_2/CO$ ratio. On the other hand, since cobalt-based catalysts have low activity toward water gas conversion, they perform Fischer-Tropsch synthesis using synthesis gas having a high molar ratio of hydrogen/carbon monoxide ($H_2/CO=1.6$-$2.2$) produced from natural gas. The iron-based catalysts for use in Fischer-Tropsch synthesis may be obtained by a melting or precipitation method, as well as by a spray drying method. It is also reported that the iron-based catalysts obtained by spray drying have improved wear resistance and improved physical strength while maintaining catalytic activity (*Industrial & Engineering Chemistry Research* 40 (2001) 1065). In addition, iron-based catalysts generally include at least one co-catalyst that helps absorption of CO or reduction of iron. Particularly, addition of potassium to a precipitated iron catalyst increases the yield of a high-molecular weight product and improves catalytic activity. Besides potassium, copper may be used as a co-catalyst for Fischer-Tropsch synthesis using iron-based catalysts in order to accelerate reduction of iron. Copper accelerates reduction of iron and is more effective in terms of the reaction rate in Fischer-Tropsch synthesis. However, since copper reduces the activity toward water gas conversion, it is not possible to maintain a ratio of $H_2/CO$ suitable for Fischer-Tropsch synthesis. To overcome this, $C^{5+}$ hydrocarbons may be prepared selectively under a high CO conversion by using, as co-catalysts, a cooper and a 1A or 2A metal element with iron-manganese using no carrier (U.S. Pat. No. 5,118,715). In the preparation of an iron catalyst, it is advantageous that the catalyst has a large specific surface area in order to disperse small metal particles and to stabilize the catalyst. Thus, a binder as a structural stabilizer may be added in combination with a co-catalyst to an iron catalyst system.

Therefore, the present disclosure provides a method for preparing synthesis gas by carrying out a combined reforming (SRM+CDR) process using a nickel-based reforming catalyst (Ni/Ce(Zr)/MgAlO$_x$) having high catalytic activity, so that the resultant synthesis gas maintains an adequate composition of carbon monoxide, carbon dioxide and hydrogen [$H_2/(2CO+3CO_2)$], and is useful for methanol synthesis and Fischer-Tropsch synthesis using an iron-based catalyst.

DISCLOSURE

Technical Problem

Under these circumstances, we have focused on the selection of a reaction condition for preparing synthesis gas having a $H_2/(2CO+3CO_2)$ molar ratio suitable for methanol synthesis or Fischer-Tropsch synthesis, as well as a catalyst for use in the reaction. The present disclosure is directed to providing a catalyst for use in a combined reforming process for methanol synthesis and a method for preparing the same, the method including: supporting Ni as an active ingredient on Ce/MgAlO$_x$ or Ce—Zr/MgAlO$_x$ as a carrier in a weight ratio of 5-20 wt % based on the carrier, followed by calcining at 600-1000° C., wherein the catalyst has a specific surface area of 80-200 m$^2$/g. We have also found that the catalyst system ensures excellent long-term performance by maintaining an adequate $H_2/(2CO+3CO_2)$ molar ratio while the catalytic activity is varied by carbon deposition, and thus ultimately improves the yield of methanol synthesis and reactivity in Fischer-Tropsch synthesis.

In one aspect, there are provided a catalyst for use in combined reforming, useful for methanol synthesis and Fischer-Tropsch synthesis, and a method for preparing the same.

In another aspect, there is provided a method for preparing synthesis gas using the same catalyst.

Technical Solution

The catalyst for use in combined reforming includes Ni, as an active ingredient, supported on Ce/MgAlO$_x$ or Ce—Zr/MgAlO$_x$ as a carrier in a weight ratio of 5-20 wt % based on the carrier, and has a specific surface area of 80-200 m$^2$/g after calcining at a temperature of 600-1000° C.

The method for preparing a catalyst for use in combined reforming includes: 1) calcining Ce or Ce—Zr carried on a MgAlO$_x$ carrier at a temperature of 600-900° C., while maintaining the amount of Ce or Ce—Zr at 3-20 wt % and the weight ratio of Ce and Zr (Zr/Ce) within a range of 0-4, to provide a Ce(Zr)/MgAlO$_x$ carrier for combined reforming; and 2) supporting Ni as an active ingredient on Ce/MgAlO$_x$ or Ce—Zr/MgAlO$_x$ as a carrier in a weight ratio of 5-20 wt % based on the carrier, followed by calcining at a temperature of 600-1000° C.

The method for preparing synthesis gas includes: carrying out a combined reforming process in which steam reforming of natural gas is performed simultaneously with carbon dioxide reforming of methane, on the catalyst obtained by reducing the above-described catalyst with hydrogen gas at a temperature of 700-1000° C., under the conditions of a reaction temperature of 800-1000° C., reaction pressure of 0.5-20 atm, space velocity of 1,000-500,000 h$^{-1}$, and a molar ratio of CH$_4$/H$_2$O/CO$_2$ of 1/1.0-2.0/0.3-0.6.

Advantageous Effects

The combined reforming of natural gas is an economical way of using carbon dioxide. Herein, steam reforming of natural gas is carried out simultaneously with carbon dioxide reforming of methane in such a manner that a predetermined ratio of carbon monoxide/carbon dioxide/hydrogen (CO/CO$_2$/H$_2$) is maintained. In this manner, it is possible to obtain synthesis gas suitable for methanol synthesis or Fischer-Tropsch synthesis. In addition, the catalyst formed of Ni/Ce(Zr)/MgAlO$_x$ is used to prepare synthesis gas, which, in turn, is applied to methanol synthesis or Fischer-Tropsch synthesis process. The catalyst is inhibited from deactivation caused by generation of cokes during the reaction as well as deactivation caused by reoxidation of nickel with water added during the reaction. Therefore, the present disclosure provides a catalyst that shows excellent activity as compared to other reported catalysts for use in combined reforming, a method for preparing the same, and a method for preparing synthesis gas using the same.

MODE FOR INVENTION

Figure 1:
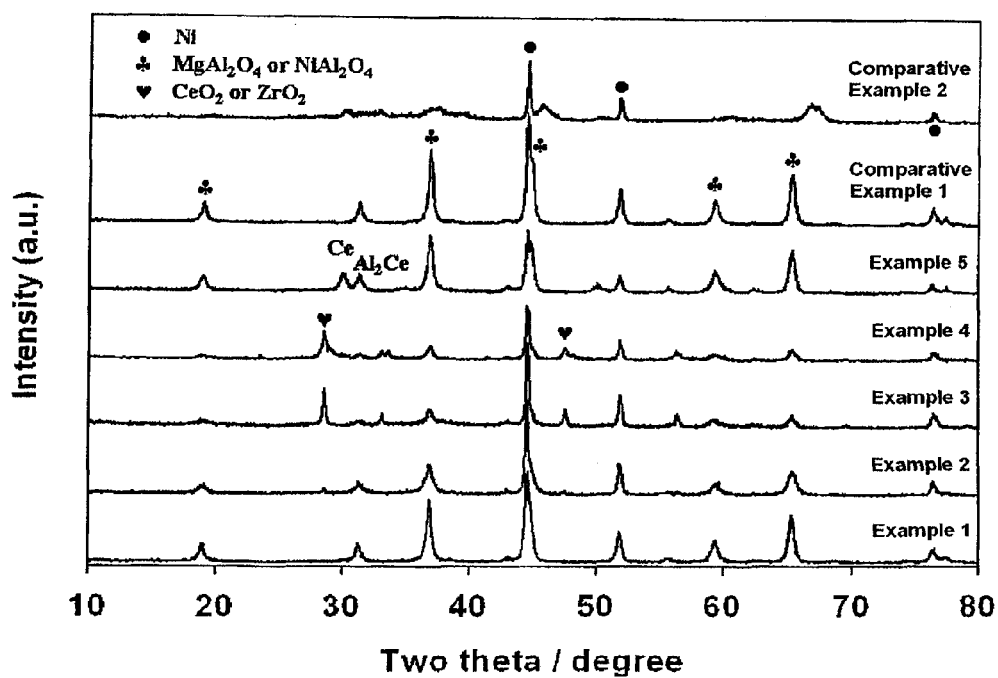
FIG. 1 shows an X-ray diffractometry (XRD) pattern of a catalyst for combined reforming disclosed herein, after reaction.

There are provided a catalyst for use in combined reforming and a method for preparing the same. The catalyst is obtained by supporting Ni as an active ingredient on Ce/MgAlO$_x$ or Ce—Zr/MgAlO$_x$ as a carrier in a weight ratio of 5-20 wt % based on the carrier, followed by calcining at 600-1000° C., and has a specific surface area of 80-200 m$^2$/g.

There is also provided a method for preparing synthesis gas using the same catalyst.

Hereinafter, this invention will be explained in more detail. The combined reforming of natural gas is an economical way of using carbon dioxide. Particularly, steam reforming of natural gas (CH$_4$) (SRM) is carried out simultaneously with carbon dioxide reforming of methane (CDR) in such a manner that a predetermined molar ratio of carbon monoxide/carbon dioxide/hydrogen (H$_2$/(2CO+3CO$_2$)=0.85-1.15) is maintained. In this manner, the catalyst (referred to also as Ni/Ce(Zr)/MgAlO$_x$) is used to prepare synthesis gas suitable for methanol synthesis or Fischer-Tropsch synthesis. As a catalyst for methanol synthesis, a catalyst system capable of minimizing formation of byproducts as disclosed in the related art (Korean Patent Application No. 2008-0072286) and other commercially available ZnO—Al$_2$O$_3$ catalysts may be used.

Generally, in SRM and CDR processes, equilibrium conversion is determined by the ratio of reactants, CH$_4$/CO$_2$/steam, reaction pressure and reaction temperature. CDR conversion decreases and carbon deposition rate increases, as the reaction pressure increases. However, in an industrial plant, reactors are downsized to reduce the initial cost requirement and reforming is carried out usually at a reaction pressure of 1.0 MPa or higher in order to reduce the cost required for the subsequent separation operation. In such combined reforming processes, CO$_2$ conversion decreases as the reaction pressure and steam amount in a feed composition increase. Thus, it is advisable to minimize the use of steam. However, this adversely affects the life of a catalyst, and thus there is a need for developing a catalyst inhibited from deactivation under the above-mentioned conditions.

To inhibit deactivation of a catalyst under the above conditions, as an economical way of using carbon dioxide, combined reforming is performed by carrying out steam reforming of natural gas simultaneously with carbon dioxide reforming of methane in such a manner that a predetermined ratio of carbon monoxide/carbon dioxide/hydrogen (H$_2$/(2CO+3CO$_2$)=0.85-1.15) is maintained. In this context, the catalyst formed of Ni/Ce(Zr)/MgAlO$_x$ is used to prepare synthesis gas suitable for methanol synthesis or Fischer-Tropsch synthesis.

The combined reforming will be explained hereinafter in more detail.

Fist, combined reforming is performed by carrying out SRM simultaneously with CDR on the catalyst formed of Ni/Ce(Zr)/MgAlO$_x$ in such a manner that a predetermined ratio of carbon monoxide/carbon dioxide/hydrogen (H$_2$/(2CO+3CO$_2$)=0.85-1.15) is maintained. In this manner, it is possible to introduce reaction conditions capable of providing high activity toward methanol synthesis and Fischer-Tropsch synthesis.

The combined reforming includes steam reforming of methane and carbon dioxide reforming of methane. To provide high activity toward methanol synthesis, the combined reforming may be realized at a molar ratio of H$_2$/(2CO+3CO$_2$) of 0.85-1.15. When the molar ratio of H$_2$/(2CO+3CO$_2$) is less than 0.85, one-pass conversion of carbon monoxide and carbon dioxide is lowered due to the lack of hydrogen. On the other hand, when the molar ratio of H$_2$/(2CO+3CO$_2$) is higher than 1.15, unreacted hydrogen may be recirculated excessively, resulting in a drop in efficiency of the overall process.

The combined reforming uses a specific catalyst formed of Ni—Ce(Zr)/MgAlO$_x$ to maintain a predetermined H$_2$/(2CO+3CO$_2$) molar ratio during the reaction by inhibiting deactivation of the catalyst caused by carbon deposition. First, hydrotalcite-like MgAlO$_x$ used as a carrier for combined reforming may be obtained by the co-precipitation method as described below or may be commercially available Mg$_2$AlO$_4$ (PURAL MG series, SASOL).

The MgAlO$_x$ carrier obtained by a co-precipitation method is used generally in the art. The MgAlO$_x$ carrier may have a specific surface area of 100-400 m$^2$/g, particularly 150-300 m$^2$/g and a molar ratio of MgO/Al$_2$O$_3$ of 0.2-0.8. When MgAlO$_x$ carrier has a specific surface area less than 100 m$^2$/g, such a small specific surface area provides reduced dispersibility of active ingredients, resulting in a drop in catalytic activity. When MgAlO$_x$ carrier has a specific surface area higher than 400 m$^2$/g, the carrier has reduced thermal stability, and thus may cause a drop in catalytic activity due to the sintering of the carrier during the preparation and reaction of the catalyst. In addition, when MgAlO$_x$ carrier has a molar ratio of MgO/Al$_2$O$_3$ of 0.2 or less, catalytic activity may be decreased due to the formation of nickel aluminate as in the case of a commercially available catalyst, Ni/Al$_2$O$_3$. When MgAlO$_x$ carrier has a molar ratio of MgO/Al$_2$O$_3$ higher than 0.8, the hydrotalcite structure formed during the high-temperature calcining process may not be stabilized and the catalyst may be deactivated.

To obtain MgAlO$_x$ carrier by a co-precipitation method, a basic precipitating agent is added to a mixture of an alumina precursor and a magnesium precursor, and co-precipitation is performed in a basic aqueous solution with pH 10, followed by aging. Then, the resultant precipitate is filtered and washed.

The alumina precursor and the magnesium precursor includes metal precursors generally known to those skilled in the art, and particular examples thereof include acetates, hydroxides or nitrates. The basic precipitating agent is also known to those skilled in the art, and particular examples thereof include sodium carbonate (Na$_2$CO$_3$), potassium carbonate (K$_2$CO$_3$), ammonium carbonate ((NH$_4$)$_2$CO$_3$) or sodium hydrogen carbonate (NaHCO$_3$).

After the co-precipitation, the catalyst is aged to provide precipitate. The aging operation may be carried out at 50-90° C. for at least 2-20 hours, particularly 2-15 hours. Within the above range of aging time, MgAlO$_x$ oxide having an adequate specific surface area and a stabilized hydrotalcite structure may be formed. When the aging temperature is lower than 50° C., it is difficult to form the structure of MgAlO$_x$ oxide. When the aging temperature is higher than 90° C., the resultant MgAlO$_x$ oxide has an increased particle size, resulting in a decrease in specific surface area. In addition, when the aging time is less than 2 hours, it is not possible to develop the structure of $MgAlO_x$ oxide sufficiently. When the aging time exceeds 20 hours, the resultant $MgAlO_x$ oxide has an increased particle size and decreased specific surface area, and thus the final catalyst provides reduced active sites, resulting in an increase in processing time and low cost-efficiency.

After the precipitate is washed, it is dried in an oven at 100° C. or higher, particularly at 100-150° C. for at least one day, and then is calcined at 500-1000° C., particularly 600-900° C. to provide a finished catalyst. Alternatively, the precipitate may be used directly for the preparation of a catalyst without calcining. When the calcining temperature is lower than 500° C., metal precursors may not be converted into oxide forms, and thus an adequate catalyst structure may not be obtained, leading to a drop in specific surface area of the carrier. When the calcining temperature is higher than 1000° C., the carrier has a decreased specific surface area due to the particle size growth and the active ingredients may not be dispersed on the carrier sufficiently, resulting in a drop in reaction rate during the combined reforming. In addition, when $MgAlO_x$ oxide is used as a carrier after it is subjected to drying only, it is possible to increase the dispersibility of catalyst particles while the active ingredients are supported on the carrier and to increase the activity during the combined reforming. However, in this case, hydrotalcite-like $MgAlO_x$ may not be converted into its spinel-type oxide form having an adequate structure. Therefore, it is important to provide an $MgAlO_x$ carrier having an equivalent ratio suitable for forming a spinel structure.

The catalyst for use in combined reforming may be obtained by using the hydrotalcite-like $MgAlO_x$ as a carrier through the following impregnation method.

First, $MgAlO_x$ is pretreated as a carrier by introducing a Ce component known to have oxygen storability or a Ce—Zr component capable of inhibiting carbon deposition through the simultaneous introduction of acid sites and base sites. In this manner, it is possible to inhibit deactivation of a catalyst caused by carbon deposition. Such pretreatment processes are based on our previous studies (Korean Patent Publication Nos. 2002-0027121, 2004-0051953 and 2002-0088213). It is reported in the patent publications that use of cerium-modified zirconia is capable of inhibiting deactivation of a catalyst caused by carbon deposition. The carrier used in the catalyst for combined reforming disclosed herein is obtained by maintaining the amount of Ce or Ce—Zr in $Ce(Zr)/MgAlO_x$ at 3-20 wt % based on the weight of $MgAlO_x$. When the amount of Ce or Ce—Zr is less than 3 wt %, it is not possible to inhibit carbon deposition sufficiently by the pretreatment. When the amount of Ce or Ce—Zr is higher than 20 wt %, pores in the carrier, $MgAlO_x$, are blocked to cause a drop in specific surface area, resulting in degradation of Ni dispersibility and a drop in catalytic activity. In addition, the pretreating agents for $MgAlO_x$ carrier, i.e., Ce and Zr metals are maintained at a weight ratio of Zr/Ce of 0-4. When Zr is used in an excessively large amount so that the ratio of Zr/Ce is higher than 4, dispersibility of the active ingredient Ni is degraded, resulting in a drop in catalytic activity.

As the precursors of Ce and Zr, precursors of each metal known to those skilled in the art may be used, and particular examples thereof include acetates, hydroxides or nitrates. More particularly, after Ce and Zr precursors are supported on the $MgAlO_x$ carrier, the obtained carrier is dried at 100-200° C., and then calcined at 600-1000° C., particularly at 700-900° C. Herein, the impregnation method is carried out in an aqueous solution or alcohol solution at a temperature of 40-90° C., and the resultant product is dried in a vacuum drier to remove the solvent via evaporation. Then, the resultant product is dried in an oven at 100° C. or higher for about 24 hours, and calcined before it is used as a catalyst.

Next, Ni as an active ingredient is further supported on the carrier for combined reforming, $Ce(Zr)/MgAlO_x$ obtained in the above-described manner in a weight ratio of 5-20 wt % based on the weight of $Ce(Zr)/MgAlO_x$ to provide a finished catalyst. Herein, as a nickel metal precursor, nickel acetate, hydroxide or nitrate may be used. More particularly, after the nickel precursor is supported on the $Ce(Zr)/MgAlO_x$ carrier, the resultant product is dried at 100-200° C., and then calcined at 600-1000° C., particularly at 700-900° C. The resultant $Ni/Ce(Zr)/MgAlO_x$ catalyst obtained as described above has a specific surface area of 80-200 $m^2/g$. When the amount of nickel supported on the carrier as an active ingredient is less than 5 wt %, the resultant catalyst shows poor activity due to the low amount of nickel having activity toward reforming. When the amount of nickel supported on the carrier is higher than 20 wt %, pores in the carrier $Ce(Zr)/MgAlO_x$ are blocked, resulting in degradation of nickel dispersibility and a drop in catalytic activity.

Another method for preparing a $Ni/Ce(Zr)/MgAlO_x$ catalyst for combined reforming includes supporting Ni on an $MgAlO_x$ carrier simultaneously with at least one metal precursor selected from Ce and Zr to provide a $Ni/Ce(Zr)/MgAlO_x$ catalyst. More particularly, Ni and at least one metal compound selected from Ce and Zr precursors are supported on a $MgAlO_x$ carrier, and the resultant product is dried at 100-200° C. and then calcined at a temperature ranging from 600 to 1000° C., particularly from 700 to 900° C. to provide a $Ni/Ce(Zr)/MgAlO_x$ catalyst having a specific surface area of 80-200 $m^2/g$.

In general, it was found that when preparing methanol, yield of methanol is improved in the presence of synthesis gas containing $CO_2$ as compared to synthesis gas merely containing CO and $H_2$. It was also found that a molar ratio of $CO/(CO+CO_2)$ of 0.6-0.8 provides a maximized yield of methanol. Based on this, in the case of a combined reforming process of SRM with CDR, it is important to maintain a predetermined ratio of carbon monoxide, carbon dioxide and hydrogen $[H_2/(2CO+3CO_2)=0.85-1.15]$ so that the resultant synthesis gas may be suitable for methanol synthesis and Fischer-Tropsch synthesis.

Therefore, in order to maintain a molar ratio of $H_2/(2CO+3CO_2)$ of 0.85-1.15 on a catalyst for combined reforming formed of $Ni-Ce(Zr)/MgAlO_x$, it is required that the reactants for reforming, i.e., $CH_4$, $H_2O$ and $CO_2$ is maintained at a molar ratio of $CH_4/H_2O/CO_2$ of 1/1.0-2.0/0.3-0.6, and the reaction temperature and pressure are maintained at 800-1000° C. and 0.5-20 atm, respectively, so that the methane conversion may be 80% or higher and the carbon dioxide conversion may be 45% or higher. In addition, it is required that a molar ratio of $H_2/(2CO+3CO_2)$ of 0.85-1.15 favorable to methanol synthesis is maintained to ensure improvement of methanol yield and process stability. According to the catalyst disclosed herein, the catalytic activity is maintained for 20 hours on stream by a change in molar ratio of $H_2/(2CO+3CO_2)$ less than 2%. When the combined reforming is carried out at a temperature lower than 800° C., the catalyst may undergo rapid deactivation due to carbon deposition caused by the Boudourd reaction ($2CO \rightarrow C+CO_2$ $\Delta H=-172$ kJ/mol). On the other hand, when the combined reforming is carried out at a temperature higher than 1000° C., selection of materials for forming a reforming unit is difficult, and the endothermic combined reforming reaction requires higher fuel consumption and shows low cost-efficiency, although methane conversion and carbon dioxide conversion are improved. In addition, the combined reforming may be carried out under a pressure ranging from ambient pressure to 20 atm. When the combined reforming is carried out under a low pressure, equilibrium conversion may be improved, but initial cost requirement is increased due to an increased volume of reactor. In this case, a high-pressure booster may be required to separate products, resulting in degradation of cost-efficiency. When the combined reforming is carried out under a high pressure of 20 atm or more, catalyst deactivation rate increases and equilibrium conversions of methane and carbon dioxide decrease. Therefore, it is required to maintain the above-defined ranges of reaction conditions.

It is required that the reactants for reforming, i.e., $CH_4$, $H_2O$ and $CO_2$ are maintained at a molar ratio of $CH_4/H_2O/CO_2$ of 1/1.0-2.0/0.3-0.6 in order to main a molar ratio of $H_2/(2CO+3CO_2)$ of 0.85-1.15 on a catalyst for combined reforming formed of $Ni—Ce(Zr)/MgAlO_x$. When $CH_4/H_2O$ molar ratio is less than 1.0, severe catalyst deactivation occurs due to carbon deposition. When the ratio is higher than 2.0, $CO_2$ conversion decreases, resulting in a drop in $CO_2$ availability. In addition, when $CH_4/CO_2$ molar ratio is less than 0.3, one-pass throughput of $CO_2$ decreases and an adequate molar ratio of $H_2/(2CO+3CO_2)$ may not be maintained. When $CH_4/CO_2$ molar ratio is higher than 0.6, $CO_2$ conversion decreases and the treatment of unreacted $CO_2$ is problematic in a reactor for preparing methanol. Thus, it is required to maintain the above-defined feed composition. In order to improve methanol yield and to ensure process stability under the above reaction conditions, it is required to maintain a molar ratio of $H_2/(2CO+3CO_2)$ in the product obtained after the combined reforming at 0.85-1.15. According to the catalyst disclosed herein, the catalytic activity is maintained for 20 hours on stream by a change in molar ratio of $H_2/(2CO+3CO_2)$ less than 2%.

The catalyst for combined reforming is reduced at a temperature of 700-1,000° C. before carrying out the reforming. The combined reforming is carried out at a temperature of 800-1,000° C. under a reaction pressure of 0.5-20 atm with a space velocity of 1,000-500,000 h$^{-1}$. After the combined reforming using the catalyst having stabilized activity, $CH_4$ conversion is 80% or higher and $CO_2$ conversion is 45% or higher.

The examples will now be described. The following examples are for illustrative purposes only and not intended to limit the scope of the present disclosure.

EXAMPLE 1

First, PURAL MG30 (available from Sasol, specific surface area: at least 250 m$^2$/g), which is an $MgAlO_x(30)$ carrier with a hydrotalcite structure having an $MgO/Al_2O_3$ ratio of 3/7, is provided as a catalyst carrier for combined reforming. Next, cerium acetate is impregnated thereto in such a manner that Ce metal is carried on the $MgAlO_x(30)$ carrier at a ratio of 4 wt %. At the same time, nickel nitrate hexahydrate (Ni$(NO_3)_2.6H_2O$) as a nickel precursor is supported on the $Ce/MgAlO_x(30)$ carrier at a weight ratio of 12 wt % based on the carrier. Then, the resultant product is agitated in a vacuum drier at 70° C. for 12 hours to remove water as a solvent, further dried in an oven at 100° C. for at least 24 hours, and then calcined at 850° C. for 6 hours to provide a finished catalyst $Ni/Ce/MgAlO_x(30)$.

The resultant catalyst has a specific surface area of 117 m$^2$/g, pore volume of 0.34 cc/g and an average pore size of 12.4 nm.

Before carrying out combined reforming, 0.5 g of the catalyst is mixed homogeneously with 34.5 g of alpha-alumina as a diluents, and the resultant mixture is introduced to a reactor made of Incolloy 800H. Then, the catalyst is reduced under hydrogen atmosphere (5 vol % $H_2/N_2$) at 700° C. for 3 hours, and a combined reforming reaction is carried out. To the reforming reactor, reactants including $CH_4$, $CO_2$, $H_2O$ and $N_2$ at a fixed molar ratio of 1:0.4:1:1 ($CH_4:CO_2:H_2O:N_2$) are introduced at a reaction temperature of 850° C. under a reaction pressure of 1.0 MPa with a space velocity of 5000 L ($CH_4$)/kg cat/hr. After the lapse of 3 hours and 20 hours on stream, each of methane and carbon dioxide conversions and $H_2/(2CO+3CO_2)$ molar ratios are averaged for 2 hours, and a change in $H_2/(2CO+3CO_2)$ molar ratio over 20 hours on stream is calculated. The results are shown in Table 1.

EXAMPLE 2

A catalyst is provided in the same manner as described in Example 1, except that PURAL MG50 (available from Sasol, specific surface area: at least 200 m$^2$/g), which is a $MgAlO_x(50)$ carrier with a hydrotalcite structure having a $MgO/Al_2O_3$ ratio of 5/5, is used to provide a finished catalyst $Ni/Ce/MgAlO_x(50)$. The resultant catalyst has a specific surface area of 117 m$^2$/g, pore volume of 0.30 cc/g and an average pore size of 13.2 nm. The catalyst is used to carry out combined reforming in the same manner as described in Example 1. After the lapse of 3 hours and 20 hours on stream, each of methane and carbon dioxide conversions and $H_2/(2CO+3CO_2)$ molar ratios are averaged for 2 hours, and a change in $H_2/(2CO+3CO_2)$ molar ratio over 20 hours on stream is calculated. The results are shown in Table 1.

EXAMPLE 3

A catalyst is provided in the same manner as described in Example 1, except that PURAL MG70 (available from Sasol, specific surface area: at least 180 m$^2$/g), which is a $MgAlO_x(70)$ carrier with a hydrotalcite structure having a $MgO/Al_2O_3$ ratio of 7/3, is used to provide a finished catalyst $Ni/Ce/MgAlO_x(70)$. The resultant catalyst has a specific surface area of 104 m$^2$/g, pore volume of 0.24 cc/g and an average pore size of 11.0 nm. The catalyst is used to carry out combined reforming in the same manner as described in Example 1. After the lapse of 3 hours and 20 hours on stream, each of methane and carbon dioxide conversions and $H_2/(2CO+3CO_2)$ molar ratios are averaged for 2 hours, and a change in $H_2/(2CO+3CO_2)$ molar ratio over 20 hours on stream is calculated. The results are shown in Table 1.

EXAMPLE 4

A catalyst is provided in the same manner as described in Example 1, except that PURAL MG30 (available from Sasol, specific surface area: at least 250 m$^2$/g), which is a $MgAlO_x(30)$ carrier with a hydrotalcite structure having a $MgO/Al_2O_3$ ratio of 3/7, is provided as a catalyst carrier for combined reforming, and then cerium acetate and zirconium nitrate are impregnated thereto in such a manner that Zr/Ce ratio is 0.25 and Ce—Zr is supported on the $MgAlO_x(30)$ carrier at a weight ratio of 18 wt % based on the carrier. At the same time, nickel nitrate hexahydrate (Ni$(NO_3)_2.6H_2O$) as a nickel precursor is supported on the $Ce—Zr/MgAlO_x(30)$ carrier at a weight ratio of 15 wt %. Then, the resultant product is agitated in a vacuum drier at 70° C. for 12 hours to remove water as a solvent, further dried in an oven at 100° C. for at least 24 hours, and then calcined at 850° C. for 6 hours to provide a finished catalyst Ni—Ce—Zr/MgAlO$_x$(30). The resultant catalyst has a specific surface area of 85 m$^2$/g, pore volume of 0.21 cc/g and an average pore size of 11.5 nm.

The catalyst is used to carry out combined reforming in the same manner as described in Example 1. After the lapse of 3 hours and 20 hours on stream, each of methane and carbon dioxide conversions and H$_2$/(2CO+3CO$_2$) molar ratios are averaged for 2 hours, and a change in H$_2$/(2CO+3CO$_2$) molar ratio over 20 hours on stream is calculated. The results are shown in Table 1.

EXAMPLE 5

First, PURAL MG30 (available from Sasol, specific surface area: at least 250 m$^2$/g), which is an MgAlO$_x$(30) carrier with a hydrotalcite structure having an MgO/Al$_2$O$_3$ ratio of 3/7, is provided as a catalyst carrier for combined reforming. In this Example, cerium acetate and zirconium nitrate are impregnated to the carrier in such a manner that Zr/Ce ratio is 3 and Ce—Zr is supported on the MgAlO$_x$(30) carrier at a weight ratio of 5 wt %. Then, the resultant product is agitated in a vacuum drier at 70° C. for 12 hours to remove water as a solvent, further dried in an oven at 100° C. for at least 24 hours, and then calcined at 900° C. for 6 hours to provide a Ce—Zr/MgAlO$_x$(30) carrier. Next, nickel is supported on the Ce—Zr/MgAlO$_x$(30) carrier at a weight ratio of 12 wt %, the resultant product is agitated in a vacuum drier at 70° C. for 12 hours to remove water as a solvent, further dried in an oven at 100° C. for at least 24 hours, and then calcined at 550° C. for 6 hours to provide a finished catalyst Ni/Ce—Zr/MgAlO$_x$(30). The resultant catalyst has a specific surface area of 96 m$^2$/g, pore volume of 0.31 cc/g and an average pore size of 16.5 nm.

The catalyst is used to carry out combined reforming in the same manner as described in Example 1. After the lapse of 3 hours and 20 hours on stream, each of methane and carbon dioxide conversions and H$_2$/(2CO+3CO$_2$) molar ratios are averaged for 2 hours, and a change in H$_2$/(2CO+3CO$_2$) molar ratio over 20 hours on stream is calculated. The results are shown in Table 1.

COMPARATIVE EXAMPLE 1

A catalyst is provided in the same manner as described in Example 1, except that PURAL MG30 (available from Sasol, specific surface area: at least 250 m$^2$/g), which is a MgAlO$_x$(30) carrier with a hydrotalcite structure having a MgO/Al$_2$O$_3$ ratio of 3/7, is used and only nickel is supported on the carrier at a weight ratio of 12 wt % to provide a finished catalyst Ni/MgAlO$_x$(30). The resultant catalyst has a specific surface area of 118 m$^2$/g, pore volume of 0.34 cc/g and an average pore size of 13.8 nm. The catalyst is used to carry out combined reforming in the same manner as described in Example 1. After the lapse of 3 hours and 20 hours on stream, each of methane and carbon dioxide conversions and H$_2$/(2CO+3CO$_2$) molar ratios are averaged for 2 hours, and a change in H$_2$/(2CO+3CO$_2$) molar ratio over 20 hours on stream is calculated. The results are shown in Table 1.

COMPARATIVE EXAMPLE 2

A catalyst is provided in the same manner as described in Example 4, except that gamma-alumina available from SASOL and having a specific surface area of 200 m$^2$/g is used as a catalyst carrier for combined reforming. Next, cerium acetate and zirconium nitrate are impregnated thereto in such a manner that Zr/Ce ratio is 0.75 and Ce—Zr is supported on the alumina carrier at a weight ratio of 5 wt %. Then, the resultant product is dried and then calcined at 900° C. for 6 hours to provide a Ce—Zr/γ-Al$_2$O$_3$ carrier. Then, nickel is supported on the Ce—Zr/γ-Al$_2$O$_3$ carrier at a weight ratio of 12 wt % by using nickel nitrate hexahydrate (Ni(NO$_3$)$_2$.6H$_2$O) as a nickel precursor. The resultant product is agitated in a vacuum drier at 70° C. for 12 hours to remove water as a solvent, further dried in an oven at 100° C. for at least 24 hours, and then calcined at 900° C. for 6 hours to provide a finished catalyst Ni/Ce—Zr/γ-Al$_2$O$_3$. The resultant catalyst has a specific surface area of 110 m$^2$/g, pore volume of 0.34 cc/g and an average pore size of 14.1 nm.

The catalyst is used to carry out combined reforming in the same manner as described in Example 1. After the lapse of 3 hours and 20 hours on stream, each of methane and carbon dioxide conversions and H$_2$/(2CO+3CO$_2$) molar ratios are averaged for 2 hours, and a change in H$_2$/(2CO+3CO$_2$) molar ratio over 20 hours on stream is calculated. The results are shown in Table 1.

TABLE 1

| | Catalyst Composition | CH$_4$ conversion/CO$_2$ conversion (carbon mol %) | | (H$_2$/2CO + 3CO$_2$) molar ratio | | Change in molar ratio of H$_2$/2(CO + 3CO$_2$) (%)[a] |
|---|---|---|---|---|---|---|
| | | After 3 h on stream | After 20 h on stream | After 3 h on stream | After 20 h on stream | |
| Ex. 1 | Ni/Ce/MgAlO$_x$ (30) | 86/59 | 84/58 | 0.87 | 0.86 | −1.15 |
| Ex. 2 | Ni/Ce/MgAlO$_x$ (50) | 85/55 | 84/59 | 0.87 | 0.86 | −1.15 |
| Ex. 3 | Ni/Ce/MgAlO$_x$ (70) | 80/45 | 80/45 | 0.85 | 0.85 | 0.00 |
| Ex. 4 | Ni—Ce—Zr/MgAlO$_x$ (30) | 84/58 | 83/56 | 0.86 | 0.86 | 0.00 |
| Ex. 5 | Ni—Ce—Zr/MgAlO$_x$ (30) | 86/56 | 85/57 | 0.87 | 0.87 | 0.00 |
| Comp. Ex. 1 | Ni/MgAlO$_x$ (30) | 81/48 | 80/42 | 0.85 | 0.83 | −2.35 |
| Comp. Ex. 2 | Ni/Ce—Zr/γ-Al$_2$O$_3$ | 73/46 | 77/52 | 0.81 | 0.83 | +2.47 |

[a] change in (H$_2$/2CO + 3CO$_2$) molar ratio is expressed as a percentage of the difference between the molar ratios after 20 hours on stream and the molar ratio after 3 hours on stream, based on the molar ratio after 3 hours on stream.

As can be seen from Table 1, the Ni/Ce(Zr)/MgAlO$_x$ catalysts for combined reforming obtained as described above (Examples 1-5) provide a stable methane conversion and carbon dioxide conversion of at least 80% and 45%, respectively. Particularly, a change in H$_2$/(2CO+3CO$_2$) molar ratio is less than 2% over 20 hours on stream and is maintained stably, thereby providing a condition favorable to methanol synthesis. On the contrary, the catalysts of Comparative Examples 1 and 2, which merely include Ni supported on a MgAlO$_x$ carrier or use Al$_2$O$_3$ as a carrier, show a severe change in H$_2$/(2CO+3CO$_2$) molar ratio under a conversion similar to Examples 1-5. This suggests that the catalysts of Comparative Examples 1 and 2 are not suitable for methanol synthesis. In addition, it can be seen that selection of an optimized condition of reaction temperature and reaction pressure is important in order to maintain H$_2$/(2CO+3CO$_2$) molar ratio at 0.85-1.15 as an optimal feed condition for methanol synthesis. Further, the synthesis gas obtained by the above-described method may be applied effectively to Fischer-Tropsch synthesis, particularly, with using an iron-based catalyst having activity toward hydrogenation of CO$_2$.

TABLE 2

| | | NiO and Ni Particle Size (nm) | | Increase in |
|---|---|---|---|---|
| | Catalyst Composition | Before reaction (NiO, 2θ = 37.2°) | After reaction (Ni, 2θ = 44.5°) | particle size (%)$^a$ |
| Ex. 1 | Ni/Ce/MgAlO$_x$ (30) | 11.3 | 16.4 | +45.1 |
| Ex. 2 | Ni/Ce/MgAlO$_x$ (50) | 12.4 | 24.1 | +94.4 |
| Ex. 3 | Ni/Ce/MgAlO$_x$ (70) | 14.7 | 28.6 | +94.6 |
| Ex. 4 | Ni—Ce—Zr/MgAlO$_x$ (30) | 11.5 | 24.0 | +108.7 |
| Ex. 5 | Ni—Ce—Zr/MgAlO$_x$ (30) | 11.7 | 16.6 | +41.9 |
| Comp. Ex. 1 | Ni/MgAlO$_x$ (30) | 11.8 | 18.0 | +52.5 |
| Comp. Ex. 2 | Ni/Ce—Zr/Y—Al$_2$O$_3$ | 14.3 | 35.2 | +146.2 |

$^a$Increase in nickel particle size is a percent ratio between NiO particle size before reaction and Ni particle size after reaction. Increase in particle size (%) = (Ni particle size − NiO particle size)/NiO particle size × 100.

Figure 2:
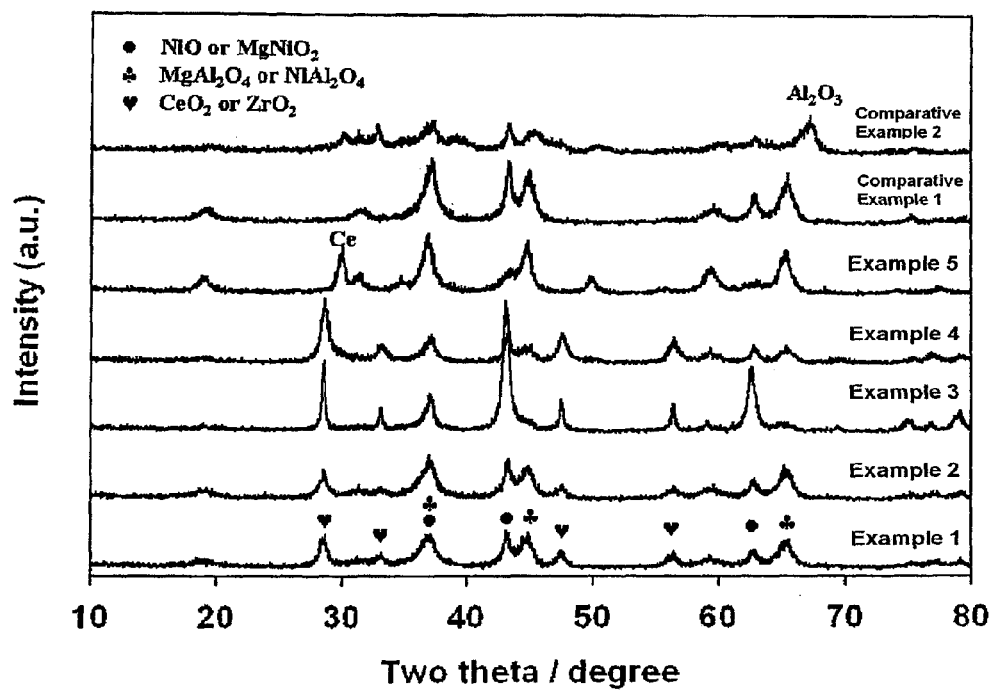
FIG. 2 shows an XRD pattern of a catalyst for combined reforming disclosed herein, before reaction on Ni/Ce(Zr)/MgAlO$_x$ catalyst in accordance with Examples shows a smaller change in nickel particle size before and after reaction, as compared to Ni/Ce—Zr/γ-Al$_2$O$_3$ of Comparative Example 2, suggesting that the catalyst, Ni/Ce(Zr)/MgAlO$_x$, maintains its activity stably.

FIG. 1, FIG. 2 and Table 2 show XRD patterns of the catalyst obtained disclosed herein before reaction and after reaction, and NiO and Ni particle sizes calculated according to the Scherrer equation by using full width at half maximum (FWHM) values at 2θ=37.2° (NiO, before reaction) and 2θ=44.5° (Ni, after reaction) in the XRD patterns. The catalysts of Examples 1-5 provide a smaller change in nickel particle size before and after reaction, as compared to Comparative Example 2, due to inhibition of sintering. This suggests that the catalysts of Examples 1-5 maintain their activities stably. In addition, Comparative Example 1 shows a small change in nickel particle size caused by sintering of nickel as an active ingredient, but causes a severe change in H$_2$/(2CO+3CO$_2$) molar ratio due to the deactivation of the catalyst during the reaction. Therefore, the catalyst of Comparative Example 1 is not suitable for applications that are covered by the catalyst disclosed herein.

INDUSTRIAL APPLICABILITY

In 2005, as a measure to deal with global warming, the Kyoto protocol is enacted about reduction of carbon dioxide emission. Accordingly, it is expected that Korea is one of the countries that owe a duty to reduce carbon dioxide after 2013. Under these circumstances, it becomes important more and more to develop technologies of reducing carbon dioxide emission and generating energy from carbon dioxide. The present disclosure provides a catalyst for combined reforming (carbon dioxide reforming of methane (CDR)+steam reforming of methane (SRM)) to produce synthesis gas, which is a process for economical utilization of carbon dioxide. The resultant synthesis gas may be applied to methanol synthesis or Fischer-Tropsch synthesis, while maintaining long-term stability. In addition, the primary product, methanol, is useful as a starting material for producing various industrial products, such as DME, DMC, biodiesel and synthetic gasoline. Further, the hydrocarbons obtained from Fischer-Tropsch synthesis may be used as chemical starting materials for various applications. Therefore, the catalyst disclosed herein is expected to contribute to development of processes for economical utilization of carbon dioxide.

The invention claimed is:
1. A method for preparing synthesis gas, comprising:
carrying out a combined reforming process of steam and carbon dioxide reforming of natural gas, which reforms natural gas with steam and carbon dioxide simultaneously, on a catalyst obtained by reducing a catalyst for natural gas reforming which reforms natural gas with steam and carbon dioxide simultaneously with hydrogen gas at a temperature of 700-1000° C., under the conditions of a reaction temperature of 850-1000° C., reaction pressure of 0.5-20 atm, space velocity of 1,000-500,000 h$^{-1}$, and a molar ratio of CH$_4$/H$_2$O/CO$_2$ of 1/1.0-2.0/0.3-0.6,
wherein the catalyst comprises Ce/MgAlO$_x$ or Ce-Zr/MgAlO$_x$, as a carrier comprising 3-20 wt % based on the carrier of Ce or Ce-Zr, respectively, carried on the MgAlO$_x$ having the weight ratio of MgO/Al$_2$O$_3$ within the range of 3/7 to 7/3; and Ni, as an active ingredient, supported on the Ce/MgAlO$_x$ or Ce-Zr/MgAlO$_x$ carrier in an amount of 5-20 wt % based on the carrier, and has a specific surface area of 80-200 m$^2$/g after calcining at a temperature of 600-1000° C.;
wherein the combined reforming process provides a CH$_4$ conversion and CO$_2$ conversion maintained at 80% or higher and 45% or higher, respectively, and a molar ratio of H$_2$(2CO+3CO$_2$) is maintained at 0.85-1.15.
2. The method for preparing synthesis gas according to claim 1, wherein the molar ratio of H$_2$/(2CO+3CO$_2$) undergoes a change less than 2% under the conditions of the combined reforming process.

* * * * *